United States Patent
Yan

[11] Patent Number: 6,066,156
[45] Date of Patent: May 23, 2000

[54] TEMPERATURE ACTIVATED ADHESIVE FOR RELEASABLY ATTACHING STENTS TO BALLOONS

[75] Inventor: John Y. Yan, Los Gatos, Calif.

[73] Assignee: Advanced Cardiovascular Systems, Inc., Santa Clara, Calif.

[21] Appl. No.: 09/266,426

[22] Filed: Mar. 11, 1999

[51] Int. Cl.⁷ .................................................. A61M 29/00
[52] U.S. Cl. ............................................. 606/192; 604/96
[58] Field of Search ................................... 606/108, 191, 606/192, 194, 96, 103

[56] References Cited

U.S. PATENT DOCUMENTS

| | | | |
|---|---|---|---|
| 4,199,646 | 4/1980 | Hori et al. . | |
| 4,880,683 | 11/1989 | Stow . | |
| 5,100,429 | 3/1992 | Sinofsky et al. . | |
| 5,156,911 | 10/1992 | Stewart . | |
| 5,158,548 | 10/1992 | Lau et al. ................................... | 604/96 |
| 5,387,450 | 2/1995 | Stewart . | |
| 5,412,035 | 5/1995 | Schmitt et al. . | |
| 5,749,880 | 5/1998 | Banas et al. ............................ | 606/198 |
| 5,817,100 | 10/1998 | Igaki ....................................... | 606/108 |
| 5,920,975 | 7/1999 | Morales ................................... | 29/282 |
| 5,944,726 | 8/1999 | Blaeser et al. ........................... | 606/108 |
| 5,968,069 | 10/1999 | Dusbabek et al. ....................... | 606/194 |
| 5,976,155 | 11/1999 | Foreman et al. ......................... | 606/108 |
| 6,004,348 | 12/1999 | Banas et al. ............................. | 623/1 |

Primary Examiner—Paul J. Hirsch
Assistant Examiner—Michael B Priddy
Attorney, Agent, or Firm—Fulwider Patton Lee & Utecht, LLP

[57] ABSTRACT

A delivery catheter, with or without an inflation balloon, and coated with a heat activated adhesive to secure a stent thereon is disclosed. The adhesive has a phase transformation temperature just above the temperature of human blood, so that below the transformation temperature the adhesive is tacky, and above the transformation temperature the adhesive is non-tacky. In a stenting procedure, when the stent is mounted to the balloon catheter and the catheter is introduced into a body lumen, the adhesive is below the transformation temperature and remains tacky to hold the stent to the catheter. Once the stent-catheter assembly is positioned at the deployment site, a warm saline or dye solution is injected to heat the adhesive to above the transformation temperature. The adhesive becomes non-tacky and releases the bond between the catheter and deployed stent allowing the former to be withdrawn.

28 Claims, 1 Drawing Sheet

TEMPERATURE ACTIVATED ADHESIVE FOR RELEASABLY ATTACHING STENTS TO BALLOONS

BACKGROUND OF THE INVENTION

The present invention relates to an apparatus for loading a tubular graft, such as a stent, onto a catheter assembly. Such a catheter assembly can be, for example, of the kind used in typical percutaneous transluminal coronary angioplasty (PTCA) procedures.

In typical PTCA procedures, a guiding catheter is percutaneously introduced into the cardiovascular system of a patient through the brachial or femoral arteries and advanced through the vasculature until the distal end of the guiding catheter is in the ostium. A guide wire and a dilatation catheter having a balloon on the distal end are introduced through the guiding catheter with the guide wire sliding within the dilatation catheter.

The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall, thereby dilating the lumen of the artery. The balloon is then deflated to a small profile, so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis may occur in the artery, which may require another angioplasty procedure, a surgical bypass operation, or some other method of repairing or strengthening the area. To reduce the likelihood of restenosis and to strengthen the area, an intravascular stent is implanted for maintaining vascular patency. The stent is typically transported through the patient's vasculature where it has a small delivery diameter, and then is expanded to a larger diameter, often by the balloon portion of the catheter. The stent also may be of the self-expanding type.

Since the catheter and stent will be traveling through the patient's vasculature, and probably through the coronary arteries, the stent must have a small, delivery diameter and must be firmly attached to the catheter until the physician is ready to implant it. Thus, the stent must be loaded onto the catheter so that it does not interfere with delivery, and it must not come off of the catheter until it is implanted in the artery.

In conventional procedures where the stent is placed over the balloon portion of the catheter, it is necessary to crimp the stent onto the balloon portion to reduce its diameter and to prevent it from sliding off the catheter when the catheter is advanced through a patient's vasculature. Non-uniform crimping can result in sharp edges being formed along the now uneven surface of the crimped stent. Furthermore, non-uniform stent crimping may not achieve the desired minimal profile for the stent and catheter assembly. Where the stent is not reliably crimped onto the catheter, the stent may slide off the catheter and into the patient's vasculature prematurely and embolize as a loose foreign body, possibly causing thrombosis. Thus, it is important to ensure the proper crimping of a stent onto a catheter in a uniform and reliable manner.

This crimping is sometimes done by hand, which can be unsatisfactory due to the uneven application of force, again resulting in non-uniform crimps. In addition, it is difficult to judge when a uniform and reliable crimp has been applied. Some self-expanding stents are difficult to load by hand onto a delivery device such as a catheter. Furthermore, the more the stent is handled, the higher the likelihood of human error which would be antithetical to crimping the stent properly. Hence, there is a need in the art for a device for reliably crimping a stent onto a catheter.

There have been mechanisms devised for loading a stent on to a catheter. For example, U.S. Pat. No. 5,437,083 to Williams et al. discloses a stent-loading mechanism for loading a stent onto a balloon delivery catheter of the kind typically used in PTCA procedures. The device comprises an arrangement of plates having substantially flat and parallel surfaces that move in rectilinear fashion with respect to each other. A stent carrying catheter can be crimped between the flat surfaces to affix the stent onto the outside of the catheter by relative motion between the plates. The plates have multiple degrees of freedom and may have force-indicating transducers to measure and indicate the force applied to the catheter while crimping of the stent.

Williams et al. also discloses a stent-loading device comprising an elongated tubular member having an open end and a sealed off end. The tubular member houses an elastic bladder which extends longitudinally along the inside of the tubular member. The tubular member and bladder are designed to hold a stent that is to be loaded onto a balloon catheter assembly. Upon placement of the stent over the balloon portion of the catheter, a valve in the loading device is activated to inflate the bladder. The bladder compresses the stent radially inward onto the balloon portion of the catheter to a reduced diameter to thus achieve a snug fit.

Although the above-described methods by which stents are crimped are simple, there is a potential for not crimping the stent sufficiently tight to prevent it from loosening in the tortuous anatomy of the coronary arteries. Because the amount of compression needed to be applied by the fingers will vary with the (a) strength of the operator, (b) day-to-day operation, (c) catheter and balloon material and configuration, (d) experience of the operator in crimping, and (e) other factors, the tightness in which the stent is crimped onto a balloon catheter may vary considerably.

Indeed, because of these factors, the tightness follows a normal or Chi square distribution. At the lower tail end of the distribution, the stents will be loose and susceptible to movement on the balloon during insertion. At the higher tail end, the stent will be too tight and will affect the expansion characteristics (i.e., a dog bone effect) of the balloon.

Currently, a majority of stents are crimped onto the balloons of PTCA delivery catheters by deformation of the stent. In these cases, there is no adhesive on the balloons. As a result, a one to three percent stent loss has been observed. If the stent detaches from the balloon, the patient may require surgery to retrieve the stent.

To minimizes the stent loss problem, some manufacturers premount or precrimp their stents onto the PTCA balloons to ensure that the stents are securely attached to the catheter. This is an extra cost to the manufacturer, and does not give the cardiologist the choice to use any type of PTCA delivery catheters. It is also an added cost to the cath lab which pays for the extra PTCA delivery catheter.

One solution has been to coat the PTCA balloons with a pressure sensitive adhesive. The adhesive anchors the stent onto the balloon of the PTCA delivery catheter. Stent loss during stenting is reduced as a result of this approach.

However, several problems arise when it is necessary to remove the balloon from the stented artery at the deployment site. First, stent apposition against the arterial wall may be affected as the catheter balloon is deflated after stent expansion. Second, as the balloon is deflated, the stent struts which are still adhered to the balloon retract with the balloon. As a result, the struts can be bent, deflected, or deformed towards the lumen of the artery. This may result in deleterious effects on the blood compatibility of the stent and affect the stent's ability to support the artery.

Third, the stent can be displaced from the lesion as the catheter is pulled out of the patent. This leads to mispositioning of the stent with respect to the lesion. The stent is no longer supporting a lesion as it was intended, but after it has shifted, is supporting a healthy portion of the artery.

Fourth, residual adhesives may be transferred onto the stent's inner surface as the balloon is physically peeled away from the stent. The presence of the residual adhesive on the metal surface may affect crossability of other catheters and guidewires. Residual adhesives left on the stent may affect the blood compatibility of the stent as well.

Another approach is disclosed in U.S. Pat. No. 5,100,429 to Sinofsky et al. This approach suggests anchoring an endovascular stent to a balloon catheter with a photodegradable adhesive. Once the stent is delivered and expanded against the arterial wall, light is directed onto the adhesive resulting in degradation of the adhesive.

A problem with using a photodegradable adhesive is that it may be released into the blood stream and tissue when the adhesive breaks down in the presence of UV light. There is also an added engineering requirement to integrate an optical fiber into the delivery catheter or some other means to expose the adhesive to light. Without this light source, the adhesive is not degraded and the stent cannot be detached from the PTCA balloon after stent expansion. Including an optical fiber to the delivery catheter not only increases costs to the manufacturer, but also makes the delivery catheter profile larger and ungainly.

In view of the foregoing, there is a need for a catheter having a facility to secure a stent thereon, yet easily releases the stent from the catheter on command at the deployment site.

SUMMARY OF THE INVENTION

The present invention is directed to a stent delivery catheter for delivering a stent, the catheter comprising a catheter body having a deflated balloon portion, a layer of heat sensitive adhesive disposed on the balloon portion, wherein the adhesive is tacky at and below a temperature T, and is non-tacky above T; and wherein the stent is disposed on the layer of heat sensitive adhesive. In the preferred embodiment, temperature T is greater than 38° C. but less than 47° C. Again in the preferred embodiment, the heat sensitive adhesive is made from a crystallizable polymer.

Because blood temperature is typically 37° C. or below, the adhesive anchors a crimped stent onto the catheter during stent delivery, thus preventing stent movement or detachment from the catheter at an inopportune or unforseen instant. Once the stent is delivered and deployed against the arterial wall, warm saline or dye solution can be injected into the blood stream to heat the adhesive to above 38° C., or preferably 40° C. to accommodate for biological variances in the blood temperature.

The rise in temperature leads to phase transformation; i.e., melting of the adhesive and subsequent changes from a tacky state to a non-tacky state. Consequently, the stent no longer adheres to the catheter. The catheter can then be withdrawn without interfering with the deployed stent.

In an alternative embodiment, the catheter includes an inflation balloon used to expand the stent. The balloon is coated with the heat sensitive adhesive while deflated and the stent is mounted thereon. Once at the deployment site, the balloon is inflated to seat the stent at the lesion in the vessel. Again, warm saline or a dye solution is injected into the blood stream to heat the adhesive to above the phase transformation temperature of the adhesive, melting the adhesive. The adhesive changes from a tacky state to a non-tacky state. The stent then no longer adheres to the balloon. The balloon can then be deflated and removed from the artery; the balloon detaches from the stent without residual bonding or adherence.

The ability of the temperature sensitive adhesive to change from tackiness to non-tackiness addresses all of the problems inherent in prior art devices. Naturally, one main function of the adhesive is to prevent movement and loss of the stent during its delivery.

After the stent is positioned at the lesion and expanded, the adhesive is no longer useful. As mentioned above, it can be made non-tacky by the cardiologist with a slight elevation in blood temperature. The slight change in blood temperature, up to 10° C. above normal body temperature, does not affect the health of the patient.

With the adhesive no longer sticking to the stent, the balloon on the delivery catheter can be easily deflated and removed without affecting the stent's apposition against the arterial wall or positioning relative to the lesion. Little or no adhesive residuals are transferred onto the stent surface, because the balloon is not pulled or peeled away from the stent.

The present invention is not limited to attaching coronary stents on catheters. Other stents used to maintain body lumens open can be attached to a balloon or a balloonless delivery catheter in the same manner. The present invention can also be applied to delivery and removal of temporary vena cava filters used to trap embolus.

The degree of tackiness or stickiness of the present invention heat activated, pressure sensitive adhesive can be varied. It may be adjusted to have greater adhesion towards the balloon and/or stent, but preferably, towards the balloon. It may be formulated to covalently bond the balloon material which are typically made from polyethylene (PE), polyethylene terephthalate (PET), or Nylon.

The phase transformation temperature of the adhesive can be adjusted depending on the adhesive formulation and chemistry. A higher temperature prevents premature change from tackiness to non-tackiness of the adhesive.

The present invention heat sensitive adhesive can be applied onto the balloon surface by various methods including brushing, wiping, spraying, dipping, or other techniques known in the art. Application of the heat sensitive adhesive to the catheter can be performed by the manufacturer or by the cardiologist in the cath lab.

In an exemplary embodiment, the thickness of the heat sensitive adhesive on the balloon can vary. It may range from 0.000010 inch to 0.005 inch thick.

In various alternative embodiments, the heat sensitive adhesive can fully coat or partially coat the balloon surface. It can be applied on the distal or proximal ends of the balloon depending on the strength of adhesion required between the stent and the balloon. If a delivery sleeve or sheath covers the balloon, such as with a C-flex sleeve covering the balloon, the coating can be applied onto the surface of the C-flex sleeve.

In an alternative method of the invention, a stent having interstitial spaces between its struts is crimped on to a catheter or a balloon portion of the catheter. Next, a heat sensitive adhesive is at least partially filled in to the interstitial spaces and bonds to the surface of the balloon or catheter. The presence of the adhesive helps maintain the stent's position on the balloon or catheter. Also, with the interstitial spaces at least partially filled in, the stent profile is much smoother. The smoother profile minimizes "fish scaling" of the stent as it is advanced through a patient's tortuous arteries.

These and other advantages of the invention will become apparent from the following detailed description thereof when taken in conjunction with the accompanying exemplary drawings.

DETAILED DESCRIPTION OF THE PREFERRED EMBODIMENTS

The present invention is directed to a stent delivery catheter that employs a temperature sensitive adhesive to bond the stent to the catheter. While the invention is described in detail as applied to use in the coronary arteries, those skilled in the art will appreciate that it can be applied to devices for use in other body lumens as well, such as peripheral arteries and veins. Also, although the invention is described with respect to mounting a stent on the balloon portion of a catheter, the invention is not so limited and includes mounting stents or grafts on any type of catheter used to deliver and implant such stents. Where different embodiments have like elements, like reference numbers have been used.

Figure 1:
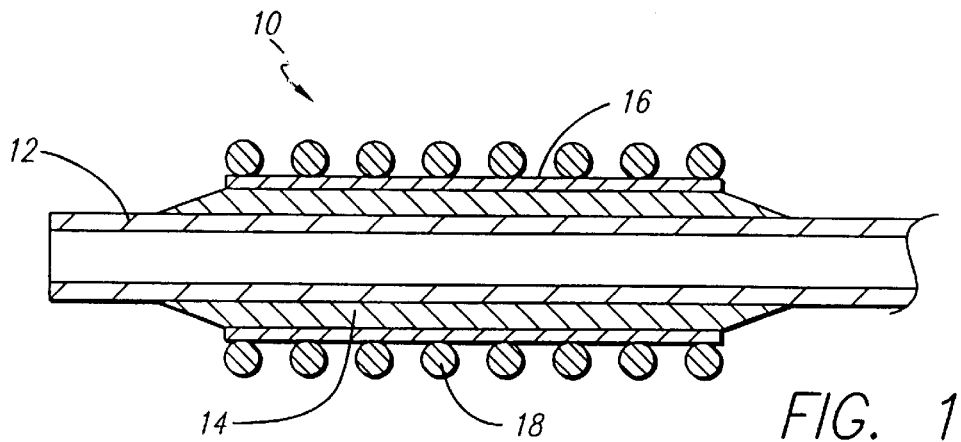
FIG. 1 is a side elevational view of a preferred embodiment of the present invention shown in a cross-section, depicting the stent, a portion of the catheter body, balloon, and heat sensitive adhesive.
Figure 2:
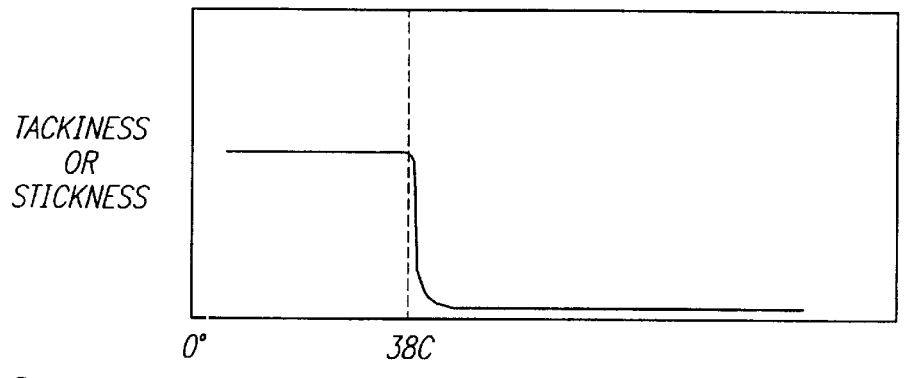
FIG. 2 is a theoretical plot of the tackiness of a temperature sensitive adhesive versus a temperature scale.

As shown in FIGS. 1 and 2, the present invention in a preferred embodiment is directed to a catheter with a temperature activated adhesive that is applied to the surface of the catheter. The performance characteristics of an exemplary temperature activated adhesive is plotted graphically in FIG. 2, where the horizontal axis represents adhesive temperature and the vertical axis represents the tackiness of the adhesive. As seen in FIG. 2, the adhesive has a sticky or tacky surface at or below, preferably, 38° C. but transforms to a non-sticky surface at temperatures above 38° C. Accordingly, the phase transformation temperature of 38° C. is represented by the vertical dashed line.

Because human blood temperature is approximately 37° C. or below, the adhesive is in its tacky state and can attach the stent on the catheter during stent delivery to prevent stent movement or detachment. Once the stent is delivered and deployed against the arterial wall, warm saline or dye solution can be injected into the blood stream to heat the adhesive to above 38° C., preferably 40° C. to accommodate for biological variances in blood temperature. The rise in temperature leads to phase transformation, and melting of the adhesive. With the rise in temperature, the adhesive changes from a tacky state to a non-tacky state. Without the tackiness in the adhesive, the stent no longer adheres to the catheter. The catheter can then be cleanly separated from the deployed stent and withdrawn from the artery with equal effectiveness as a PTCA catheter without any adhesive.

FIG. 1 depicts a preferred embodiment of the present invention showing a cross-section of a portion of catheter 10 having catheter body 12 that includes folded balloon 14. An exterior surface of balloon 14 is coated with a layer of heat sensitive adhesive 16. Stent 18 is mounted on heat sensitive adhesive 16.

Although catheter 10 is shown having balloon 14, in an alternative embodiment, the present invention contemplates a catheter without an inflation balloon. To be sure, the present invention is not limited to attaching coronary stents onto catheters. Other stents used to maintain bodily lumens open can be attached to a balloon or a balloonless delivery catheter in the same manner. The present invention also can be applied to delivery and removal of temporary vena cava filters used to trap embolus.

Stent 18 represents a typical stent design. Stents such as that shown in FIG. 1 are disclosed in, for example, U.S. Pat. No. 5,421,955 issued to Lau et al., U.S. Pat. No. 5,514,154 to Lau et al., or U.S. Pat. No. 5,649,952 to Lam.

In a preferred method of applying heat sensitive adhesive 16, the present invention contemplates applying the adhesive by various methods such as brushing, wiping, spraying, dipping, or like techniques known in the art onto the surface of catheter 10. Application of heat sensitive adhesive 16 to catheter 10 can be performed by the manufacturer or by the cardiologist in the cath lab.

Some stent manufacturers use a C-flex sleeve over the balloon on which the stent is crimped. One such manufacturer is Advanced Cardiovascular Systems, Inc., Santa Clara, Calif. If there is a C-flex sleeve (not shown) over the balloon, the adhesive can be applied to the C-flex prior to crimping the stent on the C-flex.

The layer of heat sensitive adhesive 16 preferably ranges between 0.000010 inch to 0.005 inch inclusive. In the preferred embodiment, it is less than 0.001 inch thick, but sufficiently thick to ensure stent attachment.

When heat sensitive adhesive 16 is applied and stent 18 is crimped onto balloon 14, it is important to assure that the local temperature is below the transition or phase transformation temperature of heat sensitive adhesive 16 so that it is in a tacky state. The tackiness bonds stent 18 to balloon 14. But various permutations in the process steps for applying heat sensitive adhesive 16 to balloon 14 are contemplated.

For example, it is possible to coat balloon 14 with heat sensitive adhesive 16 below the transition temperature, heat the adhesive to above the transition temperature, then mount stent 18 onto balloon 14. This permits easy mounting, alignment, and adjustment during the crimping process when stent 18 is seated to a precise location on the balloon 14. After the crimping process, the local temperature is decreased to below the phase transformation temperature of the adhesive to render it tacky again. This secures stent 18 to balloon 14 for the delivery process.

In another variation of the procedure, stent 18 may be crimped onto balloon 14 while the local temperature is below the transformation temperature so that heat sensitive adhesive 16 is tacky during the crimping process. If the adhesive is already tacky during the crimping step, there is less of a chance of introducing new stresses into the stent due to phase transformation in the adhesive.

Figure 3:
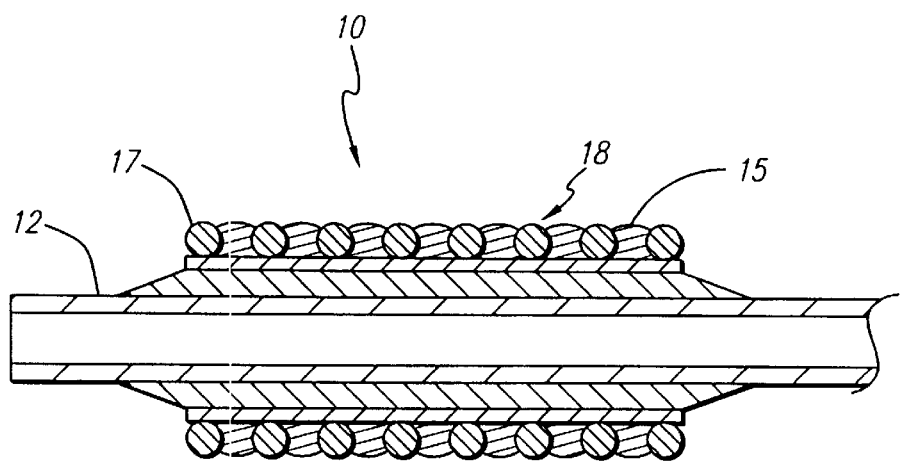
FIG. 3 is a side elevational view of a preferred embodiment, shown in cross-section, where the adhesive is applied after the stent is mounted on the balloon.

As shown in FIG. 3, another preferred method of applying the adhesive, stent 18 is first firmly crimped onto balloon 14

(or C-flex if it is used), adhesive 16 is then applied in a conventional manner so that the adhesive tends to fill the interstitial space or gaps 15 in between stent struts 17. By applying the adhesive after crimping the stent onto the balloon, there is no adhesive between the stent and balloon which should facilitate separation of the stent from the inflated balloon. Also, the adhesive filling the stent gaps makes a smoother stent profile as it is advanced through the coronary arteries, especially where tight curves are encountered. Finally, the adhesive prevents "fish scaling" which is a term referring to slight projections on the stent which develop as the stent is bent while being advanced through tortuous arteries.

The heat sensitive adhesives used in the present invention are disclosed in, for example, U.S. Pat. Nos. 5,412,035; 5,387,450; and 5,156,911, which are incorporated herein by reference thereto. Although such adhesives are intended for use in medical applications where the substrate is the skin, the adhesive compositions can be used for the present invention purposes. Indeed, such adhesives are commonly used in Band-Aids, transdermal delivery drug delivery patches, ECG electrode patches, and surgical dressing.

These heat sensitive adhesives have polyacrylate or styrene/butadiene copolymer backbone. Different functional groups are attached to the backbone. Up to 50 percent of these functional groups are crystalline in nature and can become amorphous at the phase transformation temperature (i.e., melting point of the adhesive). The degree of tack of the adhesives is less than 25 g-cm/sec below the phase transformation temperature and improves to above 100 g-cm/sec above the phase transformation temperature. Importantly, it should be noted that the reverse can also occur whereby the adhesive changes from non-tacky to tacky state when it is above its phase transformation temperature (melting point).

With the foregoing adhesives used in conjunction with the present invention stent delivery system, the ability of the temperature sensitive adhesive to change from tackiness to non-tackiness addresses all of the potential delivery problems expressed above. It is possible to use a stronger adhesive strength for the present invention heat activated adhesive, as compared to a balloon with normal pressure sensitive adhesive. The latter type adhesives should not be formulated to have too high of an adhesive strength towards the stent because it might interfere with the balloon removal after stent expansion. On the other hand, the present invention use of a heat sensitive adhesive does not have this disadvantage because its tackiness, regardless of strength, can be neutralized by application of heat.

As mentioned above, the present invention system is preferably adapted for use with a PTCA balloon catheter 10 having balloon 14 at the distal end. Of course, the present invention can be used with a balloon catheter of any conventional design known in the art as well as any catheter without a balloon. For example, a nitinol stent can be adhered to a balloonless catheter and deployed when heated above 37° C. at the same temperature the heat sensitive adhesive releases (becomes non-tacky). This eliminates the need for a protective sheath over the nitinol stent. Nitinol stents are difficult to crimp and usually require a retractable protective sheath unless the adhesive of the present invention is used. Any lubricant or lubricous coatings are removed from the exterior surface of catheter balloon 14 with a cleaning fluid such as isopropyl alcohol.

The warm saline or dye used to melt the adhesive can be injected or delivered in any conventional manner as shown, for example, in U.S. Pat. Nos. 4,641,654 to Samson et al., and 5,611,775 to Machold et al., which are incorporated herein by reference. In addition, the adhesive can be melted by a balloon catheter that includes heating elements. Such dilatation catheters with a heated balloon are shown in, for example, U.S. Pat. Nos. 5,035,694 and 5,114,423 to Kasprzyk et al., whose disclosures are incorporated herein by reference.

Other modifications can be made to the present invention without departing from the scope thereof. The specific dimensions and materials of construction are provided as examples, and substitutes are readily contemplated which do not depart from the invention.

What is claimed:

1. A stent delivery catheter for delivering a stent, comprising:

a catheter body having a shaft portion;

a layer of heat sensitive adhesive disposed on the shaft portion, wherein the adhesive is tacky at and below a temperature T, and is non-tacky above T;

wherein the stent is disposed on the layer of heat sensitive adhesive.

2. The stent delivery catheter of claim 1, wherein the shaft portion includes a balloon and the adhesive is disposed on the balloon.

3. The stent delivery catheter of claim 1, wherein temperature T is greater than 38° C. and less than 47° C.

4. The stent delivery catheter of claim 1, wherein temperature T includes a phase transformation temperature.

5. The stent delivery catheter of claim 1, wherein the layer of heat sensitive adhesive ranges between 0.000010 inch and 0.005 inch.

6. The stent delivery catheter of claim 1, wherein the heat sensitive adhesive includes a phase change from 38° to 47° C. inclusive.

7. The stent delivery catheter of claim 1, wherein the adhesive includes a crystallizable polymer.

8. The stent delivery catheter of claim 1, wherein the adhesive includes polyacrylate.

9. The stent delivery catheter of claim 1, wherein the adhesive includes styrene/butadiene.

10. The stent delivery catheter of claim 1, wherein the adhesive includes a degree of tack ranges from less than 25 g-cm/sec to greater than 100 g-cm/sec.

11. A stent delivery catheter for delivering a stent, comprising:

a catheter body having a shaft portion;

a layer of heat sensitive adhesive disposed on the shaft portion, wherein the adhesive is in a first phase at and below a temperature T, and is in a second phase above temperature T;

wherein the stent is disposed on the layer of heat sensitive adhesive.

12. The stent delivery catheter of claim 11, wherein the shaft portion includes a balloon and the adhesive is disposed on the balloon.

13. The stent delivery catheter of claim 11, wherein the adhesive is in a tacky state in the first phase, and the adhesive is in a less than tacky state in the second phase.

14. The stent delivery catheter of claim 11, wherein the adhesive is melted in the second phase.

15. A method for delivering a stent by a catheter comprising the steps of:

providing the delivery catheter with a shaft portion;

applying a heat sensitive adhesive to the shaft portion, the adhesive having a tacky state below and at a temperature T, and a less than tacky state above temperature T;

mounting the stent on the shaft portion so that the stent contacts the adhesive; and heating the adhesive to above temperature T.

16. The method of claim 15, wherein the method further comprises the steps of:

applying the adhesive to the shaft at below temperature T;

placing the catheter and stent into a vessel of a patient;

heating the adhesive to above temperature T; and withdrawing the catheter from the stent.

17. The method of claim 16, wherein the step of heating the adhesive includes injecting warm saline into the vessel.

18. The method of claim 16, wherein the step of heating the adhesive includes injecting warm dye solution into the vessel.

19. The method of claim 15, wherein the method further comprises the steps of:

providing a deflated balloon at the shaft portion;

applying the heat sensitive adhesive to the balloon at below temperature T;

mounting the stent on the balloon;

placing the catheter and stent into a vessel of a patient;

inflating and deflating the balloon to deploy the stent;

heating the adhesive to above temperature T; and withdrawing the catheter from the stent.

20. The method of claim 15, wherein temperature T is the phase transformation temperature of the adhesive.

21. A stent delivery catheter for delivering a stent having a plurality of struts with an interstitial space therebetween, comprising:

a catheter body having a shaft portion, wherein the stent is crimped on the shaft portion; and a layer of heat sensitive adhesive disposed on the shaft portion at least partially within the intertitial space of the stent, wherein the adhesive is tacky at and below a temperature T, and is non-tacky above T.

22. The stent delivery catheter of claim 21, wherein the shaft portion includes a balloon and the stent is crimped on the balloon.

23. The stent delivery catheter of claim 21, wherein temperature T is greater than 38° C. and less than 47° C.

24. The stent delivery catheter of claim 21, wherein temperature T includes a phase transformation temperature of the adhesive.

25. A method for delivering a stent having struts separated by an interstitial space on a catheter comprising the steps of:

providing the delivery catheter with a shaft portion;

crimping the stent on to the shaft portion; and applying a heat sensitive adhesive to the shaft portion to at least partially fill in the interstitial space of the stent, wherein the adhesive has a tacky state below and at a temperature T, and a less than tacky state above temperature T.

26. The method of claim 25, wherein the method further comprises the step of heating the adhesive to above temperature T.

27. The method of claim 25, wherein the method further comprises the steps of:

applying the adhesive to the shaft at below temperature T;

placing the catheter and stent into a vessel of a patient;

heating the adhesive to above temperature T; and withdrawing the catheter from the stent.

28. The method of claim 25, wherein the catheter shaft portion includes a balloon portion and the stent is crimped to the balloon portion.

* * * * *

UNITED STATES PATENT AND TRADEMARK OFFICE
CERTIFICATE OF CORRECTION

PATENT NO. : 6,066,156  
DATED : May 23, 2000  
INVENTOR(S) : John Y. Yan

Page 1 of 2

It is certified that error appears in the above-identified patent and that said Letters Patent is hereby corrected as shown below:

Column 4,
Lines 40 & 41, delete "present invention", and after "adhesive", add --of the present invention--.

Column 8, claim 1,
Line 19, after "above", add --said--.

Column 8, claim 3,
Line 25, after "wherein", add --said--.

Column 8, claim 4,
Line 27, after "wherein", add --said--.
Line 28, delete "includes", add --is--.

Column 8, claim 11,
Line 50, after "above", add --said--.

Column 8, claim 15,
Line 67, after "above", add --said--.

Column 9, claim 15,
Line 3, after "above", add --said--.

Column 9, claim 16,
Lines 6 & 8, before "temperature", add --said--.

Column 9, claim 20,
Line 19, after "wherein", add --said--.

Column 10, claim 21,
Line 2, after "above", add --said temperature--

Column 10, claim 23,
Line 6, after "wherein", add --said--.

UNITED STATES PATENT AND TRADEMARK OFFICE
CERTIFICATE OF CORRECTION

PATENT NO.   : 6,066,156
DATED         : May 23, 2000
INVENTOR(S) : John Y. Yan

It is certified that error appears in the above-identified patent and that said Letters Patent is hereby corrected as shown below:

Column 10, claim 24,
Line 9, delete "includes", add --is--.

Column 10, claim 25,
Line 19, after "above", add --said--.

Column 10, claim 26,
Line 22, after "above", add --said--.

Column 10, claim 27,
Lines 26 & 28, before "temperature" add --said--.

Signed and Sealed this

Third Day of July, 2001

*Attest:*

NICHOLAS P. GODICI
*Attesting Officer*  *Acting Director of the United States Patent and Trademark Office*